United States Patent [19]
Berry

[11] Patent Number: 5,385,138
[45] Date of Patent: Jan. 31, 1995

[54] STEREO ENDOSCOPE FOR INSERTING INTO BODY CAVITIES

[76] Inventor: Yale Berry, 134 Clinton St., Brookline, Mass. 02146

[21] Appl. No.: 179,777

[22] Filed: Jan. 10, 1994

Related U.S. Application Data

[63] Continuation of Ser. No. 823,528, Jan. 21, 1992, abandoned.

[51] Int. Cl.⁶ .................................................. A61B 1/00
[52] U.S. Cl. ...................................... 128/6; 359/368
[58] Field of Search ............... 359/434, 435, 368, 480; 385/117; 128/4, 6; 353/7

[56] References Cited

U.S. PATENT DOCUMENTS

| | | | |
|---|---|---|---|
| 3,655,259 | 4/1972 | Miyauchi et al. | 128/6 X |
| 3,776,222 | 12/1973 | Smiddy | 128/6 |
| 3,924,608 | 12/1975 | Mitsui | 128/6 X |
| 3,980,078 | 9/1976 | Tominala | 128/4 |
| 4,061,135 | 12/1977 | Widran et al. | 128/6 |
| 4,279,245 | 7/1981 | Takagi et al. | 128/4 |
| 4,593,682 | 6/1986 | Heckele | 128/6 |
| 4,651,201 | 3/1987 | Schoolman | 128/6 X |
| 4,702,571 | 10/1987 | Barber | 128/6 X |
| 4,836,188 | 6/1989 | Berry | 128/6 |
| 4,862,873 | 9/1989 | Yajima et al. | 128/6 |
| 4,924,853 | 5/1990 | Jones, Jr. et al. | 128/6 |
| 5,295,477 | 3/1994 | Janfaza | 359/368 X |

Primary Examiner—Richard J. Apley
Assistant Examiner—Beverly A. Meindl
Attorney, Agent, or Firm—Rines and Rines

[57] ABSTRACT

An endoscope having a pair of tubular side-by-side scopes contained within a body cavity, and the proximal end preferably detachably mounted on a dual prism-eyepiece housing for enabling illuminated stereoscopic viewing of the body cavity.

4 Claims, 4 Drawing Sheets

1

STEREO ENDOSCOPE FOR INSERTING INTO BODY CAVITIES

This is a continuation of Ser. No. 823,528 filed on Jan. 21, 1992 now abandoned.

The present invention relates to operating instruments for insertion into body cavities to provide the surgeon with three-dimensional or stereoscopic ("stereo") viewing capability, being more particularly directed to a stereo-endoscope apparatus.

BACKGROUND

In my earlier U.S. Pat. No. 4,836,188, techniques were developed for enabling a physician to obtain three-dimensional or stereo viewing into long thin cavities, such as the nose, mouth, vagina, ear and the like, with an appropriate head or hat-piece and light pipe "scope" supplying light, and with the field of vision enabled through the cone of light, that, unlike prior scope apparatus which enabled only one eye at a time to look into a long cavity, provided for such stereo viewing.

While also concerned with conversion from current-day two-dimensional, monocular vision to stereo viewing, the present invention, on the other hand, deals with an operating instrument that is inserted into body cavities so that operations now being performed with monocular two-dimensional vision can be performed with three-dimensional vision. The instrument is inserted, for example, into the abdomen to perform gallbladder surgery, or into the pelvis to operate on fallopian tubes, or into the sinuses to operate on the sinuses—there being many other uses as well, including in urology, operations upon a prostate and bladder, and in the tracheo-bronchial tree of the lungs, etc. While my previous stereo scope, above-described, was an apparatus that a physician wears on the head, enabling viewing along long narrow corridors of the body, the apparatus or instrument of the present invention is a working instrument that is inserted into the body and can be used to examine and enable the treatment of internal organs and also can be used to locate disease, with the instrument then being removed.

OBJECTS OF INVENTION

The present invention, therefore, has as its primary object, the provision of a stereo-viewing endoscope and the like.

Other and further objects will be explained hereinafter and are more particularly described in connection with the appended claims.

SUMMARY

In summary, however, from one of its important aspects, the invention embraces an endoscope for stereoscopic viewing within body cavities having, in combination, a longitudinally extending hollow barrel containing a pair of side-by-side longitudinally coextending tubular scopes, a coextensive illuminated fiber optic cable and a coextensive suction tube, and the terminal end of which barrel is adapted for insertion into a body cavity with the illumination carried by the fiber optic cable illuminating the same to reflect light back along each of the tubular scopes, and the suction tube aspirating the cavity; means for connecting the proximal end of the barrel to a viewing housing containing a pair of eyepieces for left and right eye viewing; and an optical system within the housing comprising a central prismatic mirror means for directing the light reflected back along the pair of tubular scopes laterally to the left and to the right sides and respective prism means associated with the respective left and right eyepieces for directing the reflected light thereto and to enable stereoscopic viewing of the illuminated cavity. Preferred and best mode embodiments and designs are later presented.

DRAWINGS

The invention will now be explained in connection with the accompanying drawings, FIG. 1 of which is an isometric view of the disassembled eyepiece-prism optical and barrel scope parts of the instrument of the invention in preferred form, with the barrel terminal end shown expanded to illustrate details;

Figure 3A:
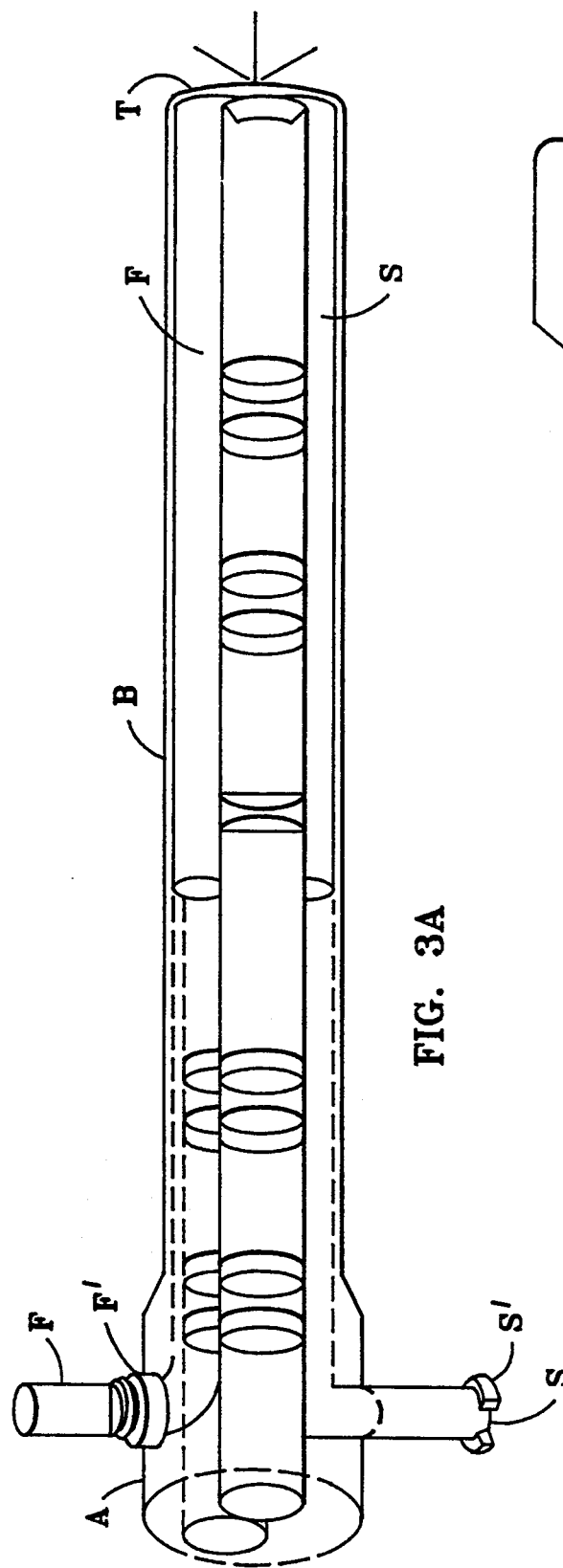
FIG. 3 is a diagrammatic view of the barrel of the scope, with the side of the housing removed to show the internal conventional scope lens structure.
Figure 3B:
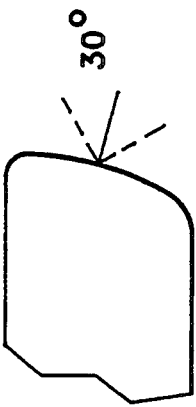
Figure 3C:
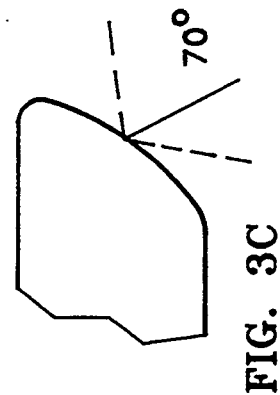
Figure 3D:
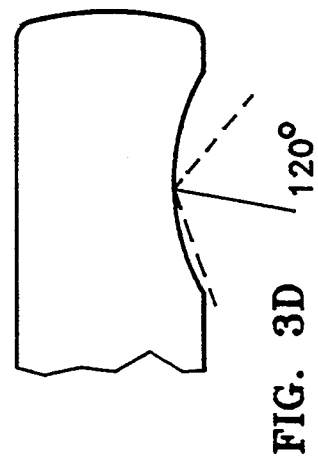
Figure 4:
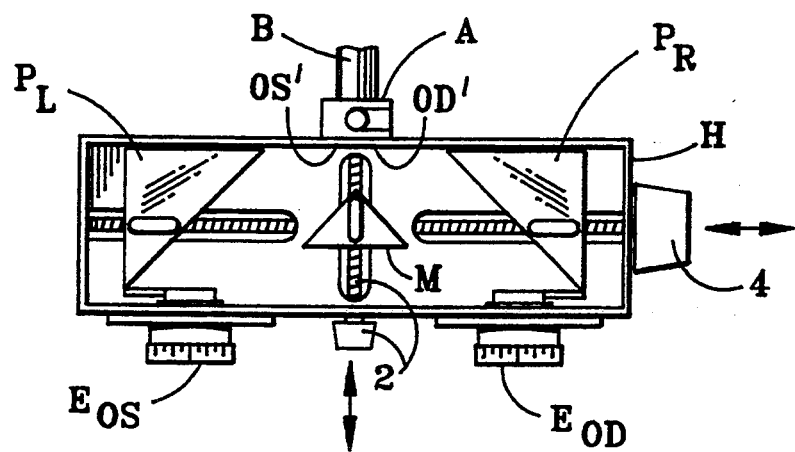
Figure 5:
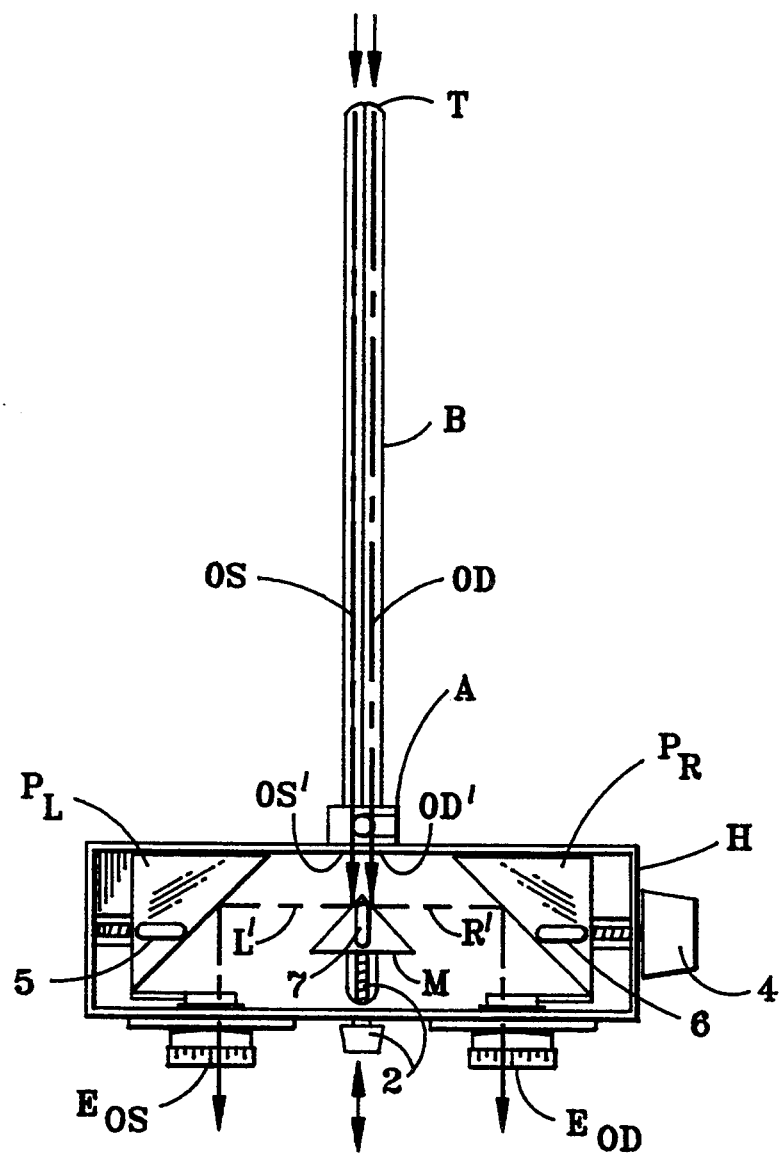
Figure 6:
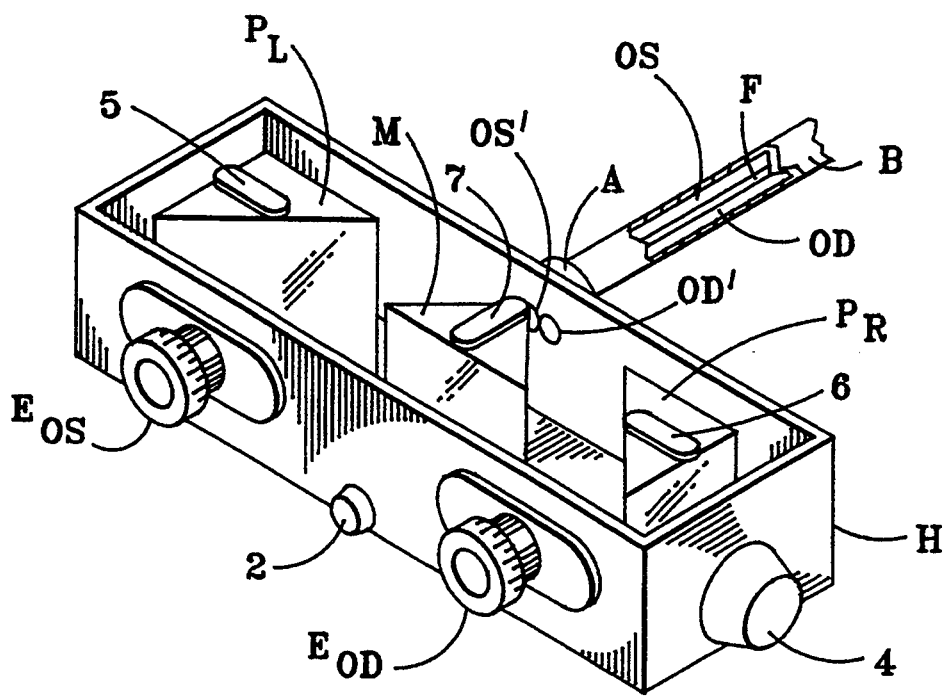

FIGS. 3A, B and C are side views of the end portions of modified barrels for different viewing angles;

FIG. 4 is a top view of the eyepiece-prism optical housing with the top cover removed;

FIG. 5 is a view similar to FIG. 4 but with the eyepiece housing connected to the barrel and with ray traces showing the stereoscopic principle;

FIG. 6 is an isometric view corresponding to FIG. 5; and

Figure 7:
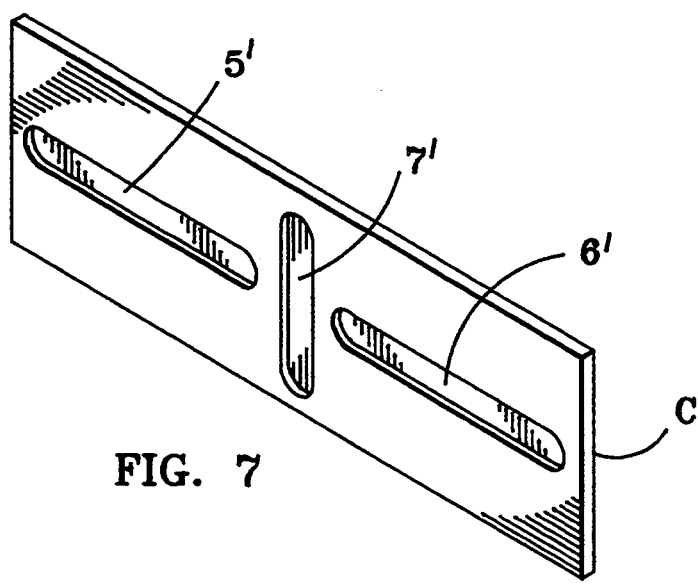

FIG. 7 is an isometric view of the eyepiece housing cover showing its inner surface construction.

DESCRIPTION OF PREFERRED EMBODIMENT(S)

Figure 1:
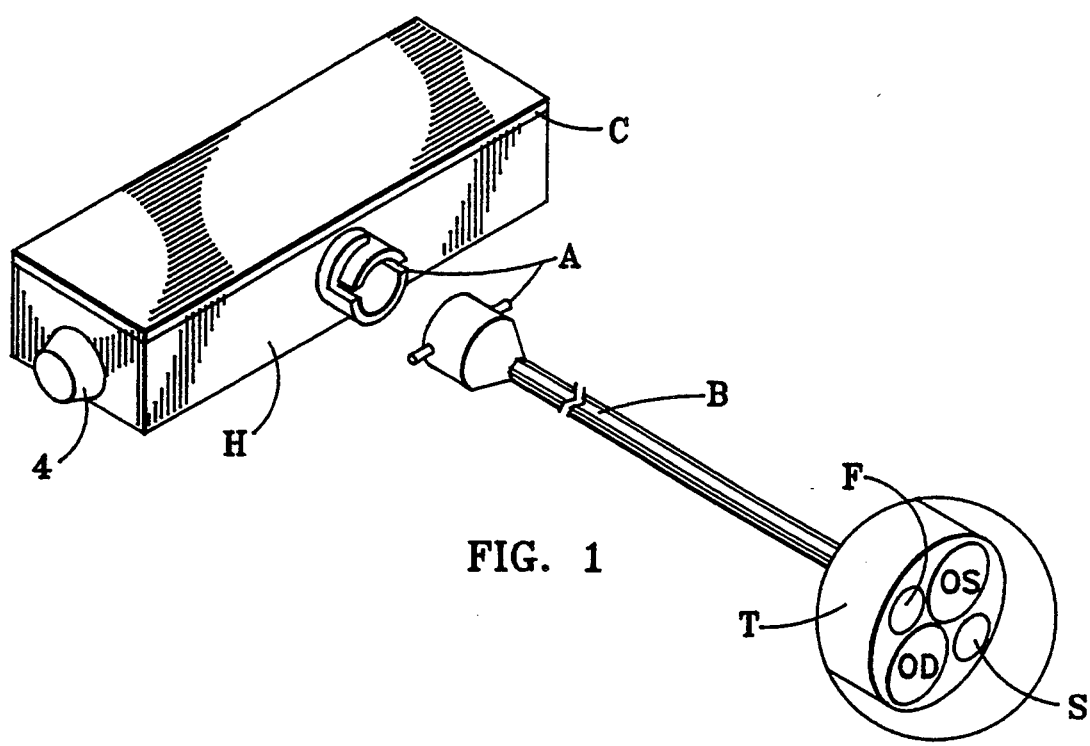
Figure 2:
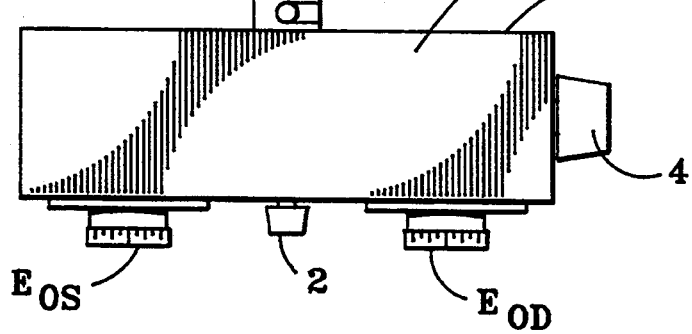
FIG. 2 is a top view of the assembled instrument.

Referring to FIGS. 1 and 2, the endoscope is shown comprising two main parts, a viewing housing H with right and left adjustable eyepieces $E_{OD}$ and $E_{OS}$ and containing prismatic optics later described for enabling stereo viewing. A barrel B extends orthogonally from the center of the housing and contains an illumination or light fiber optic channel F coextensively longitudinally extending along the barrel with a suction tube S, and the free terminal end T of which is inserted into a body cavity, as before mentioned, illuminated by light along the fiber optics cable and aspirated by the suction.

The other end of the longitudinally extending hollow barrel B is attached or removed by a twist-lock mechanism, such as a mating bayonet-type enlarged proximal end attachment A, at the central region of the front face of the housing H to permit alined light communication between the left and right coextending tubular scope paths OS and OD, FIGS. 1, 3, 5 and 6, and corresponding openings OS' and OD' in the front face of the central region of the housing front wall behind the attachment A. When the barrel B is twist-locked at A to the housing front face, FIG. 1, the tubular paths OS and OD become respectively alined as shown in FIG. 5. Light reflected from the body parts at the terminal end T of the barrel of the scope and passing along OS and OD enters through openings OS' and OD' and then reflects from the opposite inclined surfaces of a centrally disposed parametal prismatic mirror M, to the left and right, respectively, as at L' and R', FIGS. 4 and 5, to respective prisms $P_L$ and $P_R$, and thence to a pair of eyepieces $E_{OS}$ and $E_{OD}$ to enable stereoscopic viewing along the barrel B.

The prisms P$_L$ and P$_R$ reflect the field of vision toward the middle, with the central prismatic mirror M projecting the field of vision in a stereoscopic manner along the long tubular scope barrel B. The prisms P$_L$ and P$_R$ are provided with an inter-ocular threaded distance adjustment 4, FIGS. 4–6, and the central mirror M is threadedly adjustable forwardly and backwardly, by adjustment 2. At the top of each of the respective adjustable components P$_L$, P$_R$, and M, FIGS. 5 and 6, are respective raised slats or lands 5, 6 and 7, FIGS. 5 and 6, (transverse or lateral or horizontal for the former, and vertical or forward and backward along the axis of the longitudinal barrel B for the latter) which slide in respective apertures 5', 6' and 7', FIG. 7, in the housing top cover C during respective adjustments.

In effect, the tubular paths OS and OD along the barrel B constitute two side-by-side scopes. Various viewing angles can be provided to compensate for lack of mobility in certain areas of the body. Thus, in FIGS. 3A, 3B and 3C, modified terminal ends and openings are shown provided with various angles such as respectively 30°, 70° and 120° off longitudinal axis viewing. The suction tube opens to aspirate and clear the cavity for viewing. The light-carrying fiber optic cable F, moreover, may be thread-fitted at F' within the enlarged inner attachment assembly A, FIG. 3, as may the suction tube, shown with a conventional Leur lock fitting S'.

Further modifications will occur to those skilled in this art, such being considered to fall within the spirit and scope of the invention as defined .in the appended claims.

What is claimed is:

1. An endoscope for stereoscopic viewing within body cavities having, in combination, a longitudinally extending hollow barrel containing a pair of side-by-side longitudinally coextending hollow tubular scopes each defining an unfilled hollow tubular space of length substantially the same as the barrel and containing only optical lens means, a coextensive externally illuminated fiber optic cable and a coextensive suction tube, each disposed adjacent but externally of the hollow tubular scopes within the barrel and extending the length of the barrel, and the terminal end of which barrel is adapted for insertion into a body cavity with the illumination carried by the fiber optic cable illuminating the same to reflect light back along the hollow space of each of the tubular scopes,..and the suction tube aspirating the cavity; means for connecting the proximal end of the barrel to a viewing housing containing a pair of eyepieces for left and right eye viewing; and an optical system within the housing comprising a central prismatic mirror means for directing the light reflected back along the pair of tubular scopes laterally to the left and to the right sides and respective prism means associated with the respective left and right eye pieces for directing the reflected light thereto and to enable stereoscopic viewing of the illuminated cavity, and in which means is provided for adjusting each of the mirror and prism means, the mirror means forwardly and backwardly along the axis of the barrel, and the prism means laterally of the housing and eyepieces.

2. An endoscope as claimed in claim 1 and in which said connecting means is provided with means enabling the attachment and detachment of barrels containing tubular scopes with distal end regions having openings formed with different angles to enable viewing at angles off the longitudinal axis of the barrel.

3. An endoscope as claimed in claim 1 and in which the connecting means enables the barrel to be detachably connected to and removed from the front face of the viewing housing opposite the eyepieces, with said front face having a pair of openings alignable with said tubular scopes to pass light to said central mirror means.

4. An endoscope as claimed in claim 1 and in which said connecting means comprises a twist-lock connector.

* * * * *